United States Patent
Flitter et al.

(12)

(10) Patent No.: US 6,486,349 B1
(45) Date of Patent: Nov. 26, 2002

(54) AMIDE THERAPEUTICS AND METHODS FOR TREATING INFLAMMATORY BOWEL DISEASE

(75) Inventors: William D. Flitter, Mountain View, CA (US); William A. Garland, Los Gatos, CA (US); Beverly Greenwood Van-Meerveld, Oklahoma City, OK (US); Ian Irwin, Palo Alto, CA (US)

(73) Assignee: Centaur Pharmaceuticals, Inc., Sunnyvale, CA (US)

( * ) Notice: Subject to any disclaimer, the term of this patent is extended or adjusted under 35 U.S.C. 154(b) by 6 days.

(21) Appl. No.: 09/716,840

(22) Filed: Nov. 17, 2000

Related U.S. Application Data

(60) Provisional application No. 60/166,387, filed on Nov. 18, 1999.

(51) Int. Cl.⁷ ...................... A01N 37/18; A61K 31/165; C07C 233/64; C07C 233/65
(52) U.S. Cl. ........................................ 564/123; 564/183
(58) Field of Search ........................... 564/183; 514/617

(56) References Cited

U.S. PATENT DOCUMENTS 5,552,439 A * 9/1996 Panetta ........................ 514/534

OTHER PUBLICATIONS

Database CAPLUS on STN, Acc. No. 1982:142366, Morkved et al., 'Prep. and screening of some new thioacetals, sulfones, and derivatives of 4–dichloromethylbenzoyl and 4–trichloromethylbenzoyl chloride . . . ' J. Pharm. Sci. (1982). 71(1), pp. 59–63 (abstract).*

* cited by examiner

*Primary Examiner*—Brian J. Davis
(74) *Attorney, Agent, or Firm*—Burns, Doane, Swecker & Mathis, LLP

(57) ABSTRACT

Disclosed are methods for treating or preventing inflammatory bowel disease (IBD) using amide and related compounds. Pharmaceutical compositions containing amide compounds which are useful for the treatment or prophylaxis of IBD are also disclosed.

21 Claims, No Drawings

AMIDE THERAPEUTICS AND METHODS FOR TREATING INFLAMMATORY BOWEL DISEASE

This application claims priority under 35 U.S.C. §§ 119 and/or 365 to patent application Ser. No. 60/166,387 filed in U.S. on Nov. 18, 1999; the entire content of which is hereby incorporated by reference.

BACKGROUND OF THE INVENTION

1. Field of the Invention

This invention relates to the treatment of inflammatory bowel disease (IBD). More specifically, this invention is directed to methods for treating or preventing IBD using amide compounds. This invention is also directed to pharmaceutical compositions containing amide compounds which are useful for the treatment or prophylaxis of IBD.

2. State of the Art

The term inflammatory bowel disease ("IBD") describes a group of chronic inflammatory disorders of unknown causes involving the gastrointestinal tract ("GI tract"). The prevalence of IBD in the US is estimated to be about 200 per 100,000 population or approximately 500,000 people. Patients with IBD can be divided into two major groups, those with ulcerative colitis ("UC") and those with Crohn's disease ("CD").

In patients with UC, there is an inflammatory reaction primarily involving the colonic mucosa. The inflammation is typically uniform and continuous with no intervening areas of normal mucosa. Surface mucosal cells as well as crypt epithelium and submucosa are involved in an inflammatory reaction with neutrophil infiltration. Ultimately, this situation typically progresses to epithelial damage with loss of epithelial cells resulting in multiple ulcerations, fibrosis, dysplasia and longitudinal retraction of the colon.

CD differs from UC in that the inflammation extends through all layers of the intestinal wall and involves mesentery as well as lymph nodes. CD may affect any part of the alimentary canal from mouth to anus. The disease is often discontinuous, i.e., severely diseased segments of bowel are separated from apparently disease-free areas. In CD, the bowel wall also thickens which can lead to obstructions. In addition, fistulas and fissures are not uncommon.

Clinically, IBD is characterized by diverse manifestations often resulting in a chronic, unpredictable course. Bloody diarrhea and abdominal pain are often accompanied by fever and weight loss. Anemia is not uncommon, as is severe fatigue. Joint manifestations ranging from arthralgia to acute arthritis as well as abnormalities in liver function are commonly associated with IBD. Patients with IBD also have an increased risk of colon carcinomas compared to the general population. During acute "attacks" of IBD, work and other normal activity are usually impossible, and often a patient is hospitalized.

Although the cause of IBD remains unknown, several factors such as genetic, infectious and immunologic susceptibility have been implicated. IBD is much more common in Caucasians, especially those of Jewish descent. The chronic inflammatory nature of the condition has prompted an intense search for a possible infectious cause. Although agents have been found which stimulate acute inflammation, none has been found to cause the chronic inflammation associated with IBD. The hypothesis that IBD is an autoimmune disease is supported by the previously mentioned extraintestinal manifestation of IBD as joint arthritis, and the known positive response to IBD by treatment with therapeutic agents such as adrenal glucocorticoids, cyclosporine and azathioprine, which are known to suppress immune response. In addition, the GI tract, more than any other organ of the body, is continuously exposed to potential antigenic substances such as proteins from food, bacterial byproducts (LPS), etc.

Once the diagnosis has been made, typically by endoscopy, the goals of therapy are to induce and maintain a remission. The least toxic agents which patients are typically treated with are the aminosalicylates. Sulfasalazine (Azulfidine), typically administered four times a day, consists of an active molecule of aminosalicylate (5-ASA) which is linked by an azo bond to a sulfapyridine. Anaerobic bacteria in the colon split the azo bond to release active 5-ASA. However, at least 20% of patients cannot tolerate sulfapyridine because it is associated with significant side-effects such as reversible sperm abnormalities, dyspepsia or allergic reactions to the sulpha component. These side effects are reduced in patients taking olsalazine. However, neither sulfasalazine nor olsalazine are effective for the treatment of small bowel inflammation. Other formulations of 5-ASA have been developed which are released in the small intestine (e.g. mesalamine and asacol). Normally it takes 6–8 weeks for 5-ASA therapy to show full efficacy.

Patients who do not respond to 5-ASA therapy, or who have a more severe disease, are prescribed corticosteroids. However, this is a short term therapy and cannot be used as a maintenance therapy. Clinical remission is achieved with corticosteroids within 2–4 weeks, however the side effects are significant and include a Cushing goldface, facial hair, severe mood swings and sleeplessness. The response to sulfasalazine and 5-aminosalicylate preparations is poor in Crohn's disease, fair to mild in early ulcerative colitis and poor in severe ulcerative colitis. If these agents fail, powerful immunosuppressive agents such as cyclosporine, prednisone, 6-mercaptopurine or azathioprine (converted in the liver to 6-mercaptopurine) are typically tried. For Crohn's disease patients, the use of corticosteroids and other immunosuppressives must be carefully monitored because of the high risk of intra-abdominal sepsis originating in the fistulas and abscesses common in this disease. Approximately 25% of IBD patients will require surgery (colectomy) during the course of the disease.

Oxygen-derived free radicals such as HO•, the superoxide anion and other reactive oxygen species such as HOCl, have emerged as a common pathway of tissue injury in a wide variety of diseases whose underlying cause is an inappropriately vigorous and sustained immune response (failure to control or down regulate response to the initial, appropriate stimulus). Examples of other diseases, in addition to IBD and arthritis, where this mechanism appear to be the operative cause are ARDS, septic shock, asthma, diabetes, multiple sclerosis, uveitis, etc. Typically, both a cytokine-mediated immune response and a nonspecific inflammatory cascade are involved in the primary inappropriate response with both responses mediated through active oxygen species (oxidative stress). The inappropriate secondary response, also mediated through oxidative stress) may involve tissue damaging oxidation by neutrophils and tissue macrophages.

Various approaches have been taken to suppress this inappropriate inflammatory response. Small molecule inhibitors of the various leukotriene, PAF and cyclooxygenase pathways have shown only limited efficacy, perhaps because blocking only one of many pathways does not provide a sufficiently large decrease in overall oxidative stress. Another approach has been the use of antibodies or cloned receptor molecules which target specific proteins in the inflammatory cascade such as IL-1, IL-6 or TNF-α. However, this approach is practical only for acute conditions, like septic shock or ARDS, where IV administration and antibody formation against the therapeutic protein is less of a concern. For a chronic condition like IBD, an orally active small molecule that is fully active when dosed once-a-day would be the preferred method of treatment.

Another approach to mitigating the oxidative stress resulting from an inflammatory response is to employ nitrone-related therapeutics (NRTs). The prototype NRT is α-phenyl-t-butyl nitrone (PBN) shown below.

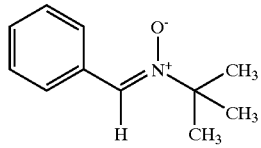

NRTs represent a new category of therapeutics with the inherent capacity to overcome the shortcomings of other previously studied compounds. Among other properties, NRTs such as PBN are believed to trap free radicals (R•) by adding the radical to form a more unreactive nitroxyl free radical.

Nitrones were first used as analytical tools capable of reacting with highly reactive radicals to yield free radical adducts that are much less reactive. In many cases, the free radical/nitrone adduct complex is stable enough to allow in vivo isolation and quantitation using electron spin resonance (ESR). The concept of using nitrones as therapeutics in, for example, neurodegenerative diseases resulted from the observations that nitrones, such as PBN, trap reactive oxygen species and/or secondary free radicals following ischemia. The therapeutic effects of nitrones may result because the nitrones convert highly reactive radicals into much less reactive products. Certain NRTs have been shown to protect experimental animals from ischemia/reperfusion injury (stroke). NRTs, administered chronically, reverse the age-associated increase in oxidatively damaged protein and the age-associated decrease in the activity of the oxidative-sensitive enzyme, glutamine synthetase, in the brain.

Accompanying the NRT-mediated changes in oxidized protein and glutamine synthetase activity is a significant improvement in the performance of animals in behavioral tests measuring short-term spatial memory. For example, it has been shown that prototype NRTs mitigate the effects of this inflammatory cascade in a number of in vivo models. Of particular interest is the consistent and well documented protection shown by PBN against the lethality induced by LPS in various rodent models of septic shock. Remarkably, PBN has also been shown to increase the life span of senescence-accelerated mice by one third, perhaps by mitigating free radical damage. PBN has also been shown to block inducible nitric oxide synthetase ("iNOS"), the enzyme responsible for producing large amounts of the highly damaging NO•. Thus, PBN can both trap HO• and suppress formation of NO•, potentially neutralizing the effects of the two agents considered to be the most damaging to tissue.

When evaluating the prospects of using an anti-oxidant to successfully treat IBD, it is perhaps also useful to consider that the anti-oxidant defense of the human colon is relatively deficient compared to human liver (mucosal levels of SOD, catalase and GSH representing 8%, 4% and 40%, respectively of liver levels), thus leaving the colon particularly sensitive to oxidative stress. A considerable number of chemical modifications have been made to increase NRTs suitability as therapeutic agents. The effects of intrinsic chemical reactivity and radical trapping ability have been examined by substituting the phenyl ring with electron donating or electron withdrawing substituents. More water soluble analogues have also been made which, for example, have a carboxylate or sodium sulfonate group on the phenyl ring. In addition, lipophilic analogues have been made with functional group substitutions on either the phenyl ring or the nitronyl nitrogen. The alkyl nitrogen substituent has also been varied through the standard straight chain and branched $C_3$–$C_5$ substituents. Nitrone isosteres and related compounds have also targeted and examined for efficacy. This approach has led to various classes of compounds, such as substituted ureas, amides, thioamides, azoxy derivatives, sulphones, and hydroxamic acids. Among these, some benzamide compounds substantially similar in structure to some nitrones, such as PBN, have been shown to have activity in the treatment of Parkinson's disease, HIV dementia, and related conditions.

As a final aspect of background, in evaluating the effectiveness of compounds in the treatment of IBD, an in vivo model based upon trinitrobenzene sulfonic acid ("TNBS") is used.

References relating to the above-mentioned subjects include:

Glickman, RM (1994) Inflammatory Bowel Disease in *Harrison's Principles of Internal Medicine* (McGraw Hill, New York, N.Y.) Chapter 255: 1403–1416.

Calkins, B M, Mendeloff, A 1 (1986) Epidemiology of Inflammatory Bowel Disease, *Epidemiology Review* 8: 60–90.

Levin, B. (1992) Inflammatory Bowel Disease and Colon Cancer, *Cancer (Supplement)*, 70: 1313–1316.

Crotty, B. (1994) Ulcerative Colitis and Xenobiotic Metabolism, *Lancet*, 343: 35–38.

Hanauer, S B, Baert, F. (1994) Medical Therapy of Inflammatory Bowel Disease, *Med Clin North Am*, 78: 1413–1426.

MacDermott, R P (1994) Alterations in the Mucosal System in Ulcerative Colitis and Crohn's Disease, *Med Clin North Am*, 78: 1207–1231.

Hanauer, B. (1993) Medical Therapy of Ulcerative Colitis, *Lancet*, 342: 412–417.

Winrow, V R, Winyard, P G, Morris, C J, Blake, D R (1993) Free radicals in Inflammation: Second Messengers and Mediators of Tissue Destruction, *Br Med Bull* 49: 506–522.

Floyd, R A and Carney, J., Nitrone Radical Traps (NRTs) Protect in Experimental Neurodegenerative Diseases, in *Neuroprotective Approaches to the Treatment of Parkinson's Disease and Other Neurodegenerative Disorders* (Olanow, C W, Jenner, P and Youssim E, Eds.) Academic Press, New York, N.Y., in press.

Cao, X. and Phillis, J W (1994) a-Phenyl-N-tert-butyl-nitrone Reduces Cortical Infarct and Edema in Rats Subjected to Focal Ischemia. *Brain Res.* 644: 267–272.

Zhao, Q., Pahlmark, K., Smith, M.-J., and Siesjo, B. (1994) Delayed Treatment with the Spin Trap a-phenyl-n-tert-butyl nitrone (PBN) Reduces Infarct Size Following Transient Middle Cerebral Artery Occlusion in Rats. *Acta Physiol. Scad.* 152: 349–350.

Oliver, C N, Starke-Reed, P E, Stadtman, E R, Carney, J M and Floyd, R A (1990) Oxidative Damage to Brain Proteins, Los of Glutamine Synthetase Activity and Production of Free Radicals During Ischemia Induced Injury to Gerbil Brain. *Proc. Natl. Acad. Sci. USA* 87: 5144–5147.

Carney, J M, Starke-Reed, P E Oliver, C N, Landrum, R W, Cheng, M S, Wu, J F and Floyd, R A (1991) Reversal or age-related increase in brain protein oxidation in enzyme activity, and loss in temporal and spatial memory by chronic administration of the spin-trapping compound N-tert-butyl-α-phenylnitrone. *Proc. Natl. Acad. Sci.*, 88: 3633–3636.

Novelli, GP (1992) Oxygen Radicals in Experimental Shock: Effects of Spin-Trapping Nitrones in Ameliorating Shock Pathophysiology, *Critical Care Medicine*, 20: 499–507.

Hamburger, S A, McCay, P B (1989) Endotoxin-Induced Mortality in Rats is Reduced by Nitrones, *Circulatory Shock*, 29: 329–334.

Progrebniak, H W, Merino, M J, Hahn, S M, Mitchell, J B, Pass, H I (1992) Spin Trap Salvage from Endotoxemia: The Role of Cytokine Down-Regulation, *Surgery*, 112: 130–139.

McKechnie, K., Furman, B L, Paratt J R (1986), Modification by Oxygen Free Radical Scavengers of the Metabolic and Cardiovascular Effects of Endotoxin Infusion in Conscious Rats, Circulatory Shock 19: 429–439.

Edamatsu,R, Mori,A., Packer, L (1995) The Spin Trap N-tert-α-phenyl-butylnitrone Prolongs the Life Span of the Senescence Accelerated Mouse, *Biochem Biophys Res Comm* 211: 847–849.

Miyajima, T., Kotake, Y. (1995) Spin Trapping Agent, Phenyl N-Tert_Butyl Nitrone, Inhibits Induction of Nitric Oxide Synthase in Endotoxin-Induced Shock in Mice, *Biochem Biophys Res Commun*, 215: 114–121.

Boettner, GR (1987) ESR Parameters of Spin Adducts, *Free Radical Biology*, 3: 259–303.

Harris, M L, Schiller, H J, Reilly, P M, Donowitz, M, Grisham, M B, Bulkley (1992), Free Radicals and Other Reactive Oxygen Metabolites in Imflammatory Bowel Disease: Cause, Consequence or Epiphenomenom, *Pharmacol. Ther.*, 53: 375–408.

Grisham M B, MacDermott, R P, Deitch E A (1990), Oxidant Defence Mechanisms in the Human Colon, *Inflammation*, 14: 669–680.

Elson, C O, Startor, R B, Tennyson, G S, Ridell, R H (1995), Experimental Models of Inflammatory Bowel Disease, *Gastroenterology*, 109: 1344–1367.

Yamada, T, Marshall, S, Specian, R D, Grisham, M B (1992) A Comparative Analysis of Two Models of Colitis in Rats, *Gastroenterology*, 102: 1524–1534.

Wallace, J A, MacNaughton, W K, Morris, G P, Beck P L (1989) Inhibition of Leulotriene Synthesis Markedly Accelerates Healing in a Rat Model of Inflammatory Bowel Disease, *Gastroenterology*, 95: 29–35.

Higa, A. McKnight, G W, Wallace, J L (1993) Attenuation of Epithelial Injury in Acute Experimental Colitis by Immunomodulators, *Eur. J. Pharmacol[<m]ed. 239: 171–178*.

Castro, G A, Roy, S A, Stockstill, R D (1974) Trichinella Spiralis: Peroxidase Activity in Isolated Cells from the Rat Intestine, *Exp. Parasitol.*, 36: 307–315.

SUMMARY OF THE INVENTION

It has now been found that certain amide compounds are effective for the treatment and prophylaxis of IBD.

Accordingly, in one of its composition a spects, this invention provides a pharmaceutical composition for the treatment or prophylaxis of inflammatory bowel disease comprising a pharmaceutically acceptable carrier and an effective inflammatory bowel disease-treating amount of a compound selected from the group consisting of:

N-tert-butyl 3-trifluoromethylbenzamide,
N-cyclopentyl 4-trifluoromethylbenzamide,
N-cyclobutyl 4-trifluoromethylbenzamide,
N-cyclopropyl 4-trifluoromethylbenzamide,
N-phenyl 4-trifluoromethylbenzamide, and pharmaceutically acceptable salts thereof.

Another aspect of this invention is directed to methods for treating a patient suffering from or susceptible to an inflammatory bowel condition. Accordingly, this invention provides a method for treating a patient suffering from or susceptible to an inflammatory bowel condition comprising administering to said patient a pharmaceutical composition comprising a pharmaceutically acceptable carrier and an effective inflammatory bowel condition-treating amount of a compound selected from the group consisting of:

N-tert-butyl 3-trifluoromethylbenzamide,
N-cyclopentyl 4-trifluoromethylbenzamide,
N-cyclobutyl 4-trifluoromethylbenzamide,
N-cyclopropyl 4-trifluoromethylbenzamide,
N-phenyl 4-trifluoromethylbenzamide, and pharmaceutically acceptable salts thereof.

In still another of its method aspects, this invention provides a method for treating or preventing inflammatory bowel disease comprising:

(a) identifying a patient suffering from or susceptible to an inflammatory bowel condition; and (b) administering to said patient a pharmaceutical composition comprising a pharmaceutically acceptable carrier and an effective inflammatory bowel condition-treating amount of a compound selected from the group consisting of:
N-tert-butyl 3-trifluoromethylbenzamide,
N-cyclopentyl 4-trifluoromethylbenzamide,
N-cyclobutyl 4-trifluoromethylbenzamide,
N-cyclopropyl 4-trifluoromethylbenzamide,
N-phenyl 4-trifluoromethylbenzamide, and pharmaceutically acceptable salts thereof.

In the methods of this invention, the pharmaceutical compositions may be administered orally, parenterally, or rectally. The methods of this invention are be effective where the inflammatory bowel condition is ulcerative colitis or Crohn's disease.

In one embodiment of the above methods, the pharmaceutical composition is preferably administered as an oral dose in an amount of from 0.1 to about 150 mg/kg of patient weight.

In another embodiment of the above methods, the pharmaceutical composition is preferably administered intravenously in an amount of from about 0.01 mg/kg/hour to about 100 mg/kg/hour of patient weight for at least about 1 hour.

In still another embodiment of the above methods, the pharmaceutical composition is preferably administered rectally in an amount of from 1 to about 150 mg/kg of patient weight.

In one of its composition aspects, this invention is also directed to novel amide compounds. Accordingly, this invention is directed to each of the following compounds:

N-tert-butyl 3-trifluoromethylbenzamide,
N-cyclopentyl 4-trifluoromethylbenzamide,
N-cyclobutyl 4-trifluoromethylbenzamide, and pharmaceutically acceptable salts thereof.

DETAILED DESCRIPTION OF THE INVENTION

The treatment methods and pharmaceutical compositions of this invention employ one or more amides or related compounds as the active agent. For the purposes of this invention, the amide compounds are named using conventional amide nomenclature, i.e., the substituents on the amide nitrogen atom are given the N- prefix. For example, N-cyclopentyl 4-trifluoromethylbenzamide has the formula:

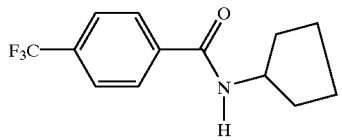

In some cases, the amides of this invention may contain one or more chiral centers. Typically, such compounds will be prepared as a racemic mixture. If desired, however, such compounds can be prepared or isolated as pure stereoisomers, i.e., as individual enantiomers or diastereomers, or as stereoisomer-enriched mixtures. All such stereoisomers (and enriched mixtures) of the amide of formula I are included within the scope of this invention. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

Definitions

When describing the compounds, pharmaceutical compositions and methods of this invention, the following terms have the following meanings unless otherwise specified.

"Trifluoromethyl" refers to the group "—$CF_3$".

"Pharmaceutically acceptable salt" refers to salts which are acceptable for administration to mammals including, by way of illustration, alkali and alkaline earth metal salts and addition salts of free acids and amines. Such pharmaceutically acceptable salts may be derived from a variety of organic and inorganic counter-ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "pharmaceutically acceptable cation" refers to a pharmaceutically acceptable cationic counterion of an acidic functional group. Such cations are exemplified by sodium, potassium, calcium, magnesium, ammonium, tetraalkylammonium cations, and the like.

General Synthetic Procedures

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protecting and deprotecting various functional groups are well known in the art. For example, numerous protecting groups, and their introduction and removal, are described in T. W. Greene and G. M. Wuts, *Protecting Groups in Organic Synthesis*, Second Edition, Wiley, New York, 1991, and references cited therein.

In a preferred method of synthesis, the amide compounds of this invention are prepared by coupling a carboxylic acid halide of formula I:

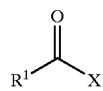

I wherein $R^1$ is 3-trifluoromethylphenyl or 4-trifluoromethylphenyl, and X is halo, preferably chloro or bromo, with an amine of formula II:

II wherein $R^2$ is tert-butyl, cyclopentyl, cyclobutyl or cyclopropyl, under conventional reaction conditions.

The coupling reaction is typically conducted by contacting the carboxylic acid halide I with an excess, preferably about 1.1 to about 3 equivalents per carbonyl halide group, of amine II. This reaction is typically conducted at a temperature of from about −10° C. to about 30° C. for about 1 to about 24 hours. Typically, the reaction is conducted in an inert diluent such as dichloromethane, chloroform, benzene, toluene, acetonitrile, tetrahydrofuran and the like.

Preferably, the coupling reaction is conducted in the presence of a suitable base to scavenge the acid generated during the reaction. Suitable bases include, by way of example, triethylamine, diisopropylethylamine, N-methylmorpholine and the like. Alternatively, an excess of amine II may be used to scavenge the acid generated during the reaction.

Upon completion of the coupling reaction, the amide is recovered by conventional methods including precipitation, chromatography, filtration, distillation and the like. If a protecting group has been employed, the protecting group is then removed using conventional procedures.

The carboxylic acid halides employed in the coupling reaction are either commercially available or can be prepared from commercially available starting materials and reagents using conventional procedures. For example, carboxylic acid halides can be readily prepared from the corresponding carboxylic acid by contacting the carboxylic acid with an inorganic acid halide, such as thionyl chloride, phosphorous trichloride, phosphorous tribromide or phosphorous pentachloride, or alternatively, with oxalyl chloride under conventional conditions. Generally, this reaction is conducted using about 1 to 5 molar equivalents of the inorganic acid halide or oxalyl chloride, either neat or in an inert solvent, such as carbon tetrachloride, at temperature in the range of about 0° C. to about 80° C. for about 1 to about 48 hours. A catalyst, such as N,N-dimethylformamide, may also be used in this reaction.

Preferred carboxylic acid halides for use in this invention include 3-trifluoromethylbenzoyl chloride and 4-trifluoromethylbenzoyl chloride.

The amines of formula II are also either known compounds or compounds that can be prepared from known starting material and reagents by conventional procedures. Examples of suitable amines for use in this reaction include, but are not limited to, tert-butylamine, cyclopentylamine, cyclobutylamine and cyclopropylamine.

Alternatively, the amides of this invention can be prepared by coupling a carboxylic acid (i.e., a compound of formula I where X is OH) with an amine of formula II using conventional coupling reagent, such as dicyclohexylcarbodiimide and the like, or N,N'-carbonyldiimidazole. This reaction can be conducted with or without the use of well known additives such as N-hydroxysuccinimide, 1-hydroxybenzotriazole, etc. which are known to facilitate the coupling of carboxylic acids and amines.

Pharmaceutical Compositions

When used as pharmaceuticals, the compounds employed in this invention are typically administered in the form of a pharmaceutical composition. Such compositions can be prepared using procedures well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The compound(s) is typically formulated into a pharmaceutical composition suitable for oral, parenteral (e.g. intravenous or intramuscular injection), or rectal (e.g. suppository) administration.

The compositions for oral administration can take the form of liquid solutions or suspensions, powders, tablets, capsules or the like. In such compositions, the amide compound is usually a minor component (0.1 to about 50% by weight) with the remainder being various vehicles or carriers and processing aids helpful for forming the desired dosing form. A liquid form may include a suitable aqueous or nonaqueous vehicle with buffers, suspending dispensing agents, colorants, flavors and the like.

A solid form may include, for example, any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, sugar, methyl salicylate, or orange flavoring.

Injectable compositions are commonly based upon injectable sterile saline or phosphate-buffered saline or other injectable carriers known in the art. Again, the active amide compound is typically a minor component, often being from about 0.05 to 10% by weight, with the remainder being the injectable carrier and the like.

Rectal administration is usually by suppository. Suppositories are generally made with a base component of cocoa butter, glycerinated gelatin, hydrogenated vegetable oils, mixtures of polyethylene glycols of various molecular weights, or fatty acid esters of polyethylene glycol. The active amide compound is usually a minor component, often from about 0.05 to 20% by weight, with the remainder being the base component.

The components for orally administrable, injectable compositions and suppositories are merely representative. Other materials as well as processing techniques and the like are set forth in Part 8 of *Remington's Pharmaceutical Sciences*, 18th edition, 1990, Mack Publishing Company, Easton, Pa., 18042, which is incorporated herein by reference.

One can also administer the compounds of the invention in sustained release forms or from sustained release drug delivery systems. A description of representative sustained release materials can be found in the incorporated materials in *Remington's Pharmaceutical Sciences*.

Conditions Treated and Treatment Regimens

The conditions treated with the pharmaceutical compositions of this invention generally include IBD and the various symptoms which fall within a definition of IBD. The formulations are administered to achieve a therapeutic effect. For those compounds that exhibit a long residency in the body, a once-a-day regimen is possible. Alternatively, multiple doses, such as up to three doses per day, typically, may offer more effective therapy. Thus, a single dose or a multidose regimen may be used.

In any event, the pharmaceutical composition is administered in such a manner so that compound is delivered into the patient's bloodstream. One excellent mode for accomplishing this is intravenous administration. Intravenous dose levels for treating IBD range from about 0.01 mg/kg/hour of active amide compound to about 100 mg/kg/hour, all for from about 1 to about 120 hours and especially 1 to 96 hours. A preloading bolus of from about 50 to about 5000 mg may also be administered to achieve adequate steady state levels. Other forms of parenteral administration, such as intramuscular injection can be used, as well. In this case, similar dose levels are employed.

With oral dosing, one to three oral doses per day, each from about 0.1 to about 150 mg/kg of active compound are employed, with preferred doses being from about 0.15 to about 100 mg/kg.

With rectal dosing, one to three rectal doses per day, each from about 1 to about 150 mg/kg of active compound are employed, with preferred doses being from about 1 to about 100 mg/kg.

In any treatment regimen, the health care professional should assess the patient's condition and determine whether or not the patient would benefit from treatment. Some degree of routine dose optimization may be required to determine an optimal doing level and pattern.

A positive dose-response relationship has been observed. As such and bearing in mind the severity of the side effects and the advantages of providing maximum possible amelioration of symptoms, it may be desired in some settings to administer large amounts of active compound, such as those described above.

The following formulation examples illustrate representative pharmaceutical compositions of this invention. The present invention, however, is not limited to the following pharmaceutical compositions.

Formulation 1—Tablets

A compound of formula I is admixed as a dry powder with a dry gelatin binder in an approximate 1:2 weight ratio. A minor amount of magnesium stearate is added as a lubricant. The mixture is formed into 240–270 mg tablets (80–90 mg of active compound per tablet) in a tablet press.

Formulation 2—Capsules

A compound of formula I is admixed as a dry powder with a starch diluent in an approximate 1:1 weight ratio. The mixture is filled into 250 mg capsules (125 mg of active compound per capsule).

Formulation 3—Liquid

A compound of formula 1(125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Injection

The compound of formula I is dissolved in a buffered sterile saline injectable aqueous medium to a concentration of approximately 5 mg/mL.

The following synthetic and biological examples are offered to illustrate this invention and are not to be construed in any way as limiting the scope of this invention.

EXAMPLES

In the examples below, all temperatures are in degrees Celsius (unless otherwise indicated). Examples 1–5 describe the synthesis of various amides; and the Bioassay Examples describe the testing of such compounds.

In the examples below, the following abbreviations have the following meanings. Abbreviations not defined below have their generally accepted meaning.

| | |
|---|---|
| bd = | broad doublet |
| bs = | broad singlet |
| d = | doublet |
| dd = | doublet of doublets |
| dec = | decomposed |
| $dH_2O$ = | distilled water |
| EtOAc = | ethyl acetate |
| EtOH = | ethanol |
| g = | grams |
| h = | hours |
| Hz = | hertz |
| L = | liter |
| m = | multiplet |
| min = | minutes |
| M = | molar |
| MeOH = | methanol |
| mg = | milligram |
| MHz = | megahertz |
| mL = | milliliter |
| mmol = | millimole |
| m.p. = | melting point |
| N = | normal |
| q = | quartet |
| quint. = | quintet |
| s = | singlet |
| t = | triplet |
| THF = | tetrahydrofuran |
| tlc = | thin layer chromatography |
| $\mu g$ = | microgram |
| $\mu L$ = | microliter |
| UV = | ultraviolet |

Example 1

Synthesis of N-tert-Butyl 3-Trifluoromethylbenzamide

To tert-butylamine (2.0 eq) in 75 mL of benzene is added 3-trifluoromethylbenzoyl chloride (1.0 eq). The temperature is maintained below 15° C. during the addition and then the reaction mixture is allowed to warm to ambient temperature and stirred for 3 hours. The solvent is then stripped and the residue is dissolved in 75 mL of dichloromethane. This solution is washed with 5% hydrochloride acid (2×75 mL), water (2×75 mL), dried over $MgSO_4$ and then the solvent is removed in vacuo to provide the title compound.

Example 2–5

Using the appropriate starting materials and the procedure described in Example 1, the following compounds were prepared:

N-cyclopentyl 4-trifluorobenzamide (Example 2),
N-cyclobutyl 4-trifluorobenzamide (Example 3),
N-cyclopropyl 4-trifluorobenzamide (Example 4),
N-phenyl 4-trifluorobenzamide (Example 5).

Bioassay Example 1

Evaluation of Compounds in TNBS Model for IBD

In this experiment, the ability of compounds of this invention to reduce colonic inflammation is demonstrated using the trinitrobenzene sulphonic acid ("TNBS") model for IBD. The TNBS model is one of the standard IBD models used in IBD discovery research and it has been extensively evaluated in rodents. See, for example, C. O. Elson et al. (1995), Experimental Models of Inflammatory Bowel Disease, *Gastroenterology*, 109: 1344–1367 and references cited therein. In this model, a single enema of TNBS induces a prolonged colonic inflammatory response (up to several weeks) that is transmural and is accompanied by oxidative damage as evidenced by an increase in myeloperoxidase ("MPO") activity. Additionally, the inflammation is characterized by discrete areas of acute necrosis, inflammation and muscle thickening. Agents with anti-inflammatory effects in patients with IBD show efficacy in this model. Although the mechanism by which TNBS induces an inflammatory response is unknown, it is thought to have an immunological basis.

Induction of Colitis

Male Sprague-Dawley rats (200–310 g) were housed in standard cages (2 per cage) and fed rat chow and tap water ad libitum. After an overnight fast, rats were brought into the laboratory and randomized into treatment groups. Colitis was induced by intrarectal administration of 0.5 ml of TNBS solution (50 mg/kg in 25–50% ethanol) using a 1 mL syringe attached to a 5–8 cm polyethylene catheter. Control animals received saline (0.9%) or a 1% methyl cellulose suspension at identical time points.

Tissue Analysis

Three days after TNBS administration, the rats were sacrificed and the colons excised and opened longitudinally. In 5 cm segments of colon, gross morphology was determined using the following scale:

| Grade | Finding |
|---|---|
| 0 | No damage |
| 1 | One area of Inflammation (red), no ulcers |
| 2 | Ulcers, no area of inflammation |
| 3 | Ulcers, one area of inflammation |
| 4 | More than 2 ulcers, inflammation at one site |
| 5 | More than 2 ulcers, inflammation > 1 cm |
| 6 | More than 2 ulcers, inflammation > 2 cm |

The weights of each 5 cm colonic segment were also recorded to assess inflammatory induced edema.

Dosing Regimen

Each of the compounds from Examples 1–5 were tested in the TNBS model at 10 mg/kg p.o. (oral) dosing. Each of the test compounds was administered by oral gavage as a 1% carboxy methyl cellulose ("CMC") suspension 1 hour prior to the administration of TNBS. Control rats were given CMC only.

Results

Each of the test compounds reduced TNBS-induced damage compared to the controls by an amount ranging from about 20% to about 50% (average scores).

Bioassay Example 2

Mouse Dextran Sulfate IBD Model

Another model used for screening candidate IBD-treating compounds is the Dextran Sulfate ("DSS") model. Similar to the TNBS model, DSS induced colitis is widely used as a screening tool for IBD therapeutics. When administered orally, DSS induces IBD-like symptoms in Swiss-Webster mice. This model can be used to determine the effectiveness of compounds of this invention when such compounds are administered orally (p.o.).

Individually housed 30–40 g male Swiss-Webster mice (B & K Universal, Fremont, Calif.) receive 3% DSS (Sigma Chemicals, St. Louis, Mo.) in their drinking water for 7 days. All animals receive food and water ad libitum.

Two groups of mice are dosed orally with either the test compound in a dosing vehicle (1% methyl cellulose, dose range of 10 mg/kg to 30 mg/kg) or dosing vehicle alone (control). Dosing is done 1 day before DSS, 1 hour before DSS and/or 5 days after start of DSS.

Clinical signs of colitis are assessed by a disease activity index ("DAI") consisting of changes in stool characteristics, fecal occult bleeding and body weight loss. The DAI is very similar to the Crohn's Disease Activity Index used in clinical trials to evaluate new agents to prevent/treat IBD. The DAI data are analyzed using Proc Anova in SAS with a Bonferoni post-hoc analysis, and Model 108 in WinNonlin™ (Professional Version 1.5, Scientific Consulting, Apex, N.C.) for the $ED_{50}$ and $E_{max}$ values. The wet weight and myeloperoxidase ("MPO") data (collected only on Day 7) are analyzed by Proc TTest in SAS. MPO is a marker for neutrophil infiltration. The following criteria are employed in this assay:

DAI Scoring (Daily)

Stool Characteristic: 0=normal, 2=loose and 4=diarrhea

Fecal Occult Blood: 0=negative, 2=positive, 4=gross bleeding

Weight Change: 0=0–1%, 1=1 to <5%, 2=5% to <10%, 3=10 to <20%, 4=>20%

MPO (Day 7 Only)

Two strips of colonic tissue/mouse

MPO activity by spectrophotometric assay

Bioassay Example 3

Establishment of the Dose-response Characteristics in the Mouse Dextran Sulfate Model To determine the dose-response relationship of a test compound in the DSS Mouse Model, the following procedure is used.

Experimental conditions and statistical analyses are the same as the Mouse Dextran Sulfate IBD Model, except four groups of mice (n=8–10/group) are used. Animals are dosed orally with either test compound (3, 10 or 30 mg/kg) or vehicle alone. In addition, the following procedure is introduced to evaluate the histology in the animals:

Histology Score

5–6 slices/segment with 15–18 total pieces/colon Score for extent of damage: 0=1–25% involvement, 1=26–50% involvement, 2=51–75% involvement, 3=76–100% involvement Score for grade:

0=intact crypt, 1=loss of ⅓ crypt, 2=loss of ⅔ crypt, 3=loss of entire crypt with surface epithelium intact, 4=loss of entire crypt and erosion of surface epithelium Score for Severity:

0=normal, 1=focal inflammatory cell infiltrate including PMNs, 2=inflammatory cell infiltration, gland dropout and crypt abscess, 3=mucosal ulceration Single evaluator (qualified pathologist) blinded to the treatment conditions.

Bioassay Example 4

Effect of Test Compounds on Flux of Reactive Oxygen Species Induced by TNF-α

Oxidative stress agents (OSA) are thought to be involved in cell death in IBD and are key initiator in the cascade of events leading to apoptosis. The purpose of this study is to evaluate the effect of a test compound on cytokine-induced OSA flux.

To visualize OSA, the dye dihydrodichlorofluorescein diacetate is used. This non-fluorescent dye is taken up by cells and deacetylated to its non-fluorescent congener dihydrodichlorofluorescein ($H_2DCF$), which is trapped within cells. Reactive oxygen species ("ROS") react with $H_2DCF$, converting it to the highly fluorescent DCF. DCF fluorescence can be measured spectrofluorometrically and can also be visualized in intact cells using fluorescent microscopy.

SK-N-MC cells (American Type Culture Collection, Rockville, Md.) are plated at 250,000 cells/well in 24-well Corning plates. Following plating, the cells are maintained in retinoic acid medium (5 $\mu$M) for five days and then treated with a test compound at 100$\mu$M for 1 hour prior to TNF-α (3.0 ng/mL) treatment. TNF-α and $H_2DCF$ are added simultaneously and cultures are incubated for an additional 4 hours. Following incubation, cultures are read in a cytofluorometer at 485–530 nm wavelength to detect increased DCF formation. Relative fluorescence units (RFU) values for the respective treatment conditions are compared. In this assay, higher fluorescence readings indicate ROS production. Thus, reductions in fluorescence indicates reduction in ROS production.

Bioassay Example 5

Effect of Compound A on TNF-α Induced Apoptosis in a Human Cell Model

This test is used to evaluate the potential of a test compound to prevent TNF-α induced apoptosis.

A test compound is evaluated in an in vitro model of TNF-α induced toxicity (see Pulliam et al. *J. Neurosci. Res.* 21:521–530 (1998)). In this model, human brain cell aggregates from fetal tissue are treated with TNF-αwhich caused an apoptotic cell death. Brain cell aggregates prepared from 1 brain were incubated for 10–12 days before experimentation. Aggregates are weighed out (100 mg/flask) and aliquoted into 10 mL flasks. TNF-α is used at a concentration of 1 ng. The test compound is added 1 hour prior to the TNF-α. Experiments include untreated brain aggregates, TNF-α-treated brain aggregates, TNF-α-+test compound treated aggregates and test compound treated aggregates. After TNF-α is added, aggregates are incubated for an additional 48 h. After this time, brain aggregates are centrifuged for 5 min at 500 rpm. The supernatant is removed and the pellet is lysed for determination of programmed cell death (Boeringer Mannheim Cell Death Kit ELISA).

Bioassay Example 6

Effect of Test Compound on TNF-α Induced Reduction in bcl-2

Cytokine-mediated apoptosis or programmed cell death is believed to be involved in a number of diseases including IBD. Reductions in bcl-2 are a major signal in initiation of the apoptotic cascade (see Jourd' heuil et al., J. Clin Gastroenterol. 25(Suppl):S61–S72 (1997)). The purpose of this study is to investigate the effects of a test compound on bcl-2 protein levels in a cellular model of cytokine mediated apoptosis.

SK-N-MC cells (American Type Culture Collection, Rockville, Md.) are plated at 500,000 cells/plate and treated with retinoic acid ("RA") (5 $\mu$M) for 5 days. Following RA treatment, the cells are incubated with a test compound (100 $\mu$M) for 1 hour. Cells are then treated with increasing concentrations of TNF-α (0, 0.3 and 3 ng/mL) for 6 h. The cells are harvested and lysed and bcl-2 is measured in the lysate using an ELISA assay (Boehringer Manheim). Quantification of bcl-2 is based on a standard curve and results are expressed as units/mL of bcl-2 in the sample.

What is claimed is:

1. A pharmaceutical composition for the treatment or prophylaxis of inflammatory bowel disease comprising a pharmaceutically acceptable carrier and an effective inflammatory bowel disease-treating amount of a compound selected from the group consisting of:

N-tert-butyl 3-trifluoromethylbenzamide,
   N-cyclopentyl 4-trifluoromethylbenzamide,
   N-cyclobutyl 4-trifluoromethylbenzamide,
   N-cyclopropyl 4-trifluoromethylbenzamide, and pharmaceutically acceptable salts thereof.

2. The pharmaceutical composition of claim 1 wherein the compound is N-tert-butyl 3-trifluoromethylbenzamide and pharmaceutically acceptable salts thereof.

3. The pharmaceutical composition of claim 1 wherein the compound is N-cyclopentyl 4-trifluoromethylbenzamide and pharmaceutically acceptable salts thereof.

4. The pharmaceutical composition of claim 1 wherein the compound is N-cyclobutyl 4-trifluoromethylbenzamide and pharmaceutically acceptable salts thereof.

5. The pharmaceutical composition of claim 1 wherein the compound is N-cyclopropyl 4-trifluoromethylbenzamide and pharmaceutically acceptable salts thereof.

6. A method for treating a patient suffering from or susceptible to an inflammatory bowel condition comprising administering to said patient a pharmaceutical composition comprising a pharmaceutically acceptable carrier and an effective inflammatory bowel condition-treating amount of a compound selected from the group consisting of:

N-tert-butyl 3-trifluoromethylbenzamide,
   N-cyclopentyl 4-trifluoromethylbenzamide,
   N-cyclobutyl 4-trifluoromethylbenzamide,
   N-cyclopropyl 4-trifluorobenzamide,
   N-phenyl 4-trifluoromethylbenzamide, and pharmaceutically acceptable salts thereof.

7. The method of claim 6 wherein the compound is N-tert-butyl 3-trifluoromethylbenzamide and pharmaceutically acceptable salts thereof.

8. The method of claim 6 wherein the compound is N-cyclopentyl 4-trifluoromethylbenzamide and pharmaceutically acceptable salts thereof.

9. The method of claim 6 wherein the compound is N-cyclobutyl 4-trifluoromethylbenzamide and pharmaceutically acceptable salts thereof.

10. The method of claim 6 wherein the compound is N-cyclopropyl 4-trifluoromethylbenzamide and pharmaceutically acceptable salts thereof.

11. The method of claim 6 wherein the compound is N-phenyl 4-trifluoromethylbenzamide and pharmaceutically acceptable salts thereof.

12. The method of claim 6 wherein said pharmaceutical composition is administered orally.

13. The method of claim 6 wherein said pharmaceutical composition is administered parenterally.

14. The method of claim 6 wherein said pharmaceutical composition is administered rectally.

15. The method of claim 6 wherein said inflammatory bowel condition is ulcerative colitis.

16. The method of claim 6 wherein said inflammatory bowel condition is Crohn's disease.

17. The method of claim 6 wherein said pharmaceutical composition is administered as an oral dose in an amount of from 0.1 to about 150 mg/kg of patient weight.

18. The method of claim 6 wherein said pharmaceutical composition is administered intravenously in an amount of from about 0.01 mg/kg/hour to about 100 mg/kg/hour of patient weight for at least about 1 hour.

19. The method of claim 6 wherein said pharmaceutical composition is administered rectally in an amount of from 1 to about 150 mg/kg of patient weight.

20. A method for treating or preventing inflammatory bowel disease comprising:

(a) identifying a patient suffering from or susceptible to an inflammatory bowel condition; and
   (b) administering to said patient a pharmaceutical composition comprising a pharmaceutically acceptable carrier and an effective inflammatory bowel condition-treating amount of a compound selected from the group consisting of:
      N-tert-butyl 3-trifluoromethylbenzamide,
      N-cyclopentyl 4-trifluoromethylbenzamide,
      N-cyclobutyl 4-trifluoromethylbenzamide,
      N-cyclopropyl 4-trifluoromethylbenzamide,
      N-phenyl 4-trifluoromethylbenzamide, and pharmaceutically acceptable salts thereof.

21. A compound selected from the group consisting of:

N-tert-butyl 3-trifluoromethylbenzamide,
   N-cyclopentyl 4-trifluoromethylbenzamide,
   N-cyclobutyl 4-trifluoromethylbenzamide, and pharmaceutically acceptable salts thereof.

* * * * *